(12) United States Patent
Wallow et al.

(10) Patent No.: US 7,858,276 B2
(45) Date of Patent: Dec. 28, 2010

(54) METHOD FOR DETERMINING SUITABILITY OF A RESIST IN SEMICONDUCTOR WAFER FABRICATION

(75) Inventors: Thomas Wallow, San Carlos, CA (US); Bruno M. LaFontaine, Pleasanton, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 731 days.

(21) Appl. No.: 11/825,448

(22) Filed: Jul. 6, 2007

(65) Prior Publication Data
US 2009/0011524 A1 Jan. 8, 2009

(51) Int. Cl.
*G03F 9/00* (2006.01)
*G03C 5/00* (2006.01)

(52) U.S. Cl. .................. 430/30; 430/296; 430/330; 430/942; 382/145

(58) Field of Classification Search ............... 430/30, 430/296, 330, 942; 382/145
See application file for complete search history.

(56) References Cited

U.S. PATENT DOCUMENTS

| 5,763,124 | A  | * | 6/1998 | Koizumi et al. ............... 430/30 |
| 7,642,102 | B2 | * | 1/2010 | Funk et al. .................... 438/14 |
| 2004/0005507 | A1 | * | 1/2004 | Lakkapragada et al. ....... 430/30 |

* cited by examiner

*Primary Examiner*—Christopher G Young
(74) *Attorney, Agent, or Firm*—Farjami & Farjami LLP

(57) ABSTRACT

In one disclosed embodiment, the present method for determining resist suitability for semiconductor wafer fabrication comprises forming a layer of resist over a semiconductor wafer, exposing the layer of resist to patterned radiation, and determining resist suitability by using a scatterometry process prior to developing a lithographic pattern on the layer of resist. In one embodiment, the semiconductor wafer is heated in a post exposure bake process after scatterometry is performed. In one embodiment, the patterned radiation is provided by an extreme ultraviolet (EUV) light source in a lithographic process. In other embodiments, patterned radiation is provided by an electron beam, or ion beam, for example. In one embodiment, the present method determines out-gassing of a layer of resist during exposure to patterned radiation.

19 Claims, 5 Drawing Sheets

METHOD FOR DETERMINING SUITABILITY OF A RESIST IN SEMICONDUCTOR WAFER FABRICATION

TECHNICAL FIELD

The present invention is generally in the field of semiconductor devices. More particularly, the invention is in the field of fabrication of semiconductor wafers.

BACKGROUND ART

During semiconductor wafer fabrication, light can be utilized in a lithographic process to enable transfer of very small lithographic patterns, such as nanometer-scale lithographic patterns, from a lithographic mask to a semiconductor wafer. In a common lithographic process, for example, light from a lithographic light source is used to transfer a pattern formed on a lithographic mask, to a semiconductor wafer, by exposing a layer of resist formed over the semiconductor wafer to emitted light that has been reflected from the lithographic mask.

A conventional approach to evaluating the suitability of a resist in semiconductor wafer fabrication involves the use of scatterometry as a post hoc metrology procedure, performed after development of a transferred lithographic pattern. Typically, light from a scatterometry light source is scattered from the surface of a patterned semiconductor wafer, and the wavelength and polarization of that scattered light are compared to unscattered light from the same source. Changes observed in the scattered light correspond in a predictable way to characteristics of the developed lithographic pattern. In this way scatterometry is conventionally used to confirm the dimensions of a transferred lithographic pattern.

By performing scatterometry measurements late in the process, e.g. after development of the resist pattern, conventional techniques often result in an unnecessary consumption of resources used in the intervening fabrication steps, when it is discovered that, for example, due to poor characteristics of resist, a desired high resolution pattern has not been properly formed.

SUMMARY

A method for determining suitability of a resist in semiconductor wafer fabrication, substantially as shown in and/or described in connection with at least one of the figures, as set forth more completely in the claims.

DETAILED DESCRIPTION OF THE INVENTION

The present invention is directed to a method for determining suitability of a resist in semiconductor wafer fabrication. The following description contains specific information pertaining to the implementation of the present invention. One skilled in the art will recognize that the present invention may be implemented in a manner different from that specifically discussed in the present application. Moreover, some of the specific details of the invention are not discussed in order not to obscure the invention. The specific details not described in the present application are within the knowledge of a person of ordinary skill in the art.

The drawings in the present application and their accompanying detailed description are directed to merely exemplary embodiments of the invention. To maintain brevity, other embodiments of the present invention, which use the principles of the present invention, are not specifically described in the present application and are not specifically illustrated by the present drawings.

Figure 1:
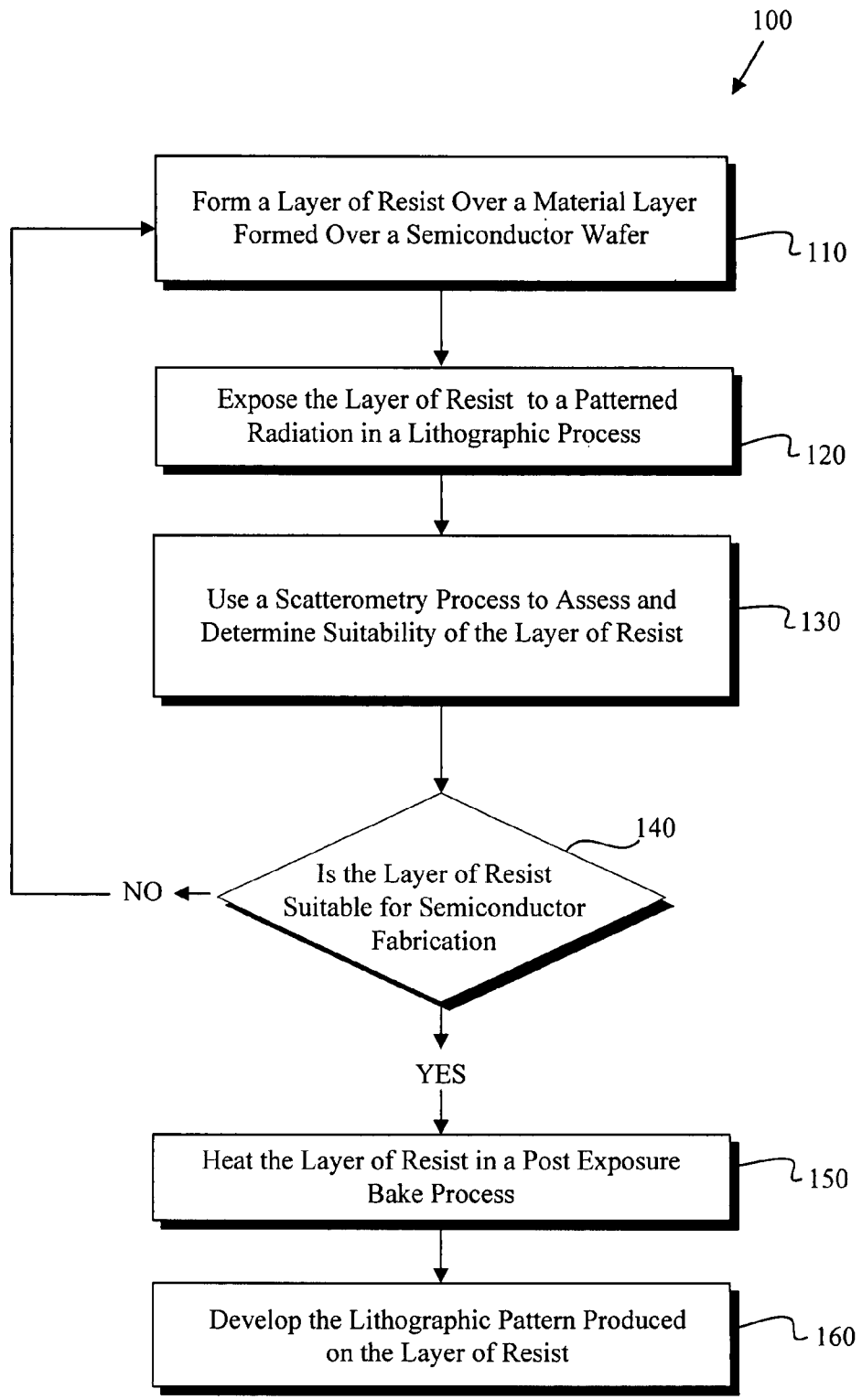
FIG. 1 shows a flowchart of an exemplary method to implement an embodiment of the present invention.

FIG. 1 shows a flowchart illustrating an exemplary method according to an embodiment of the present invention. Certain details and features have been left out of flowchart 100 that are apparent to a person of ordinary skill in the art. For example, a step may comprise one or more substeps or may involve specialized equipment or materials, as known in the art. While steps 110 through 160 indicated in flowchart 100 are sufficient to describe one embodiment of the present invention, other embodiments of the invention may utilize steps different from those shown in flowchart 100.

Figure 2A:
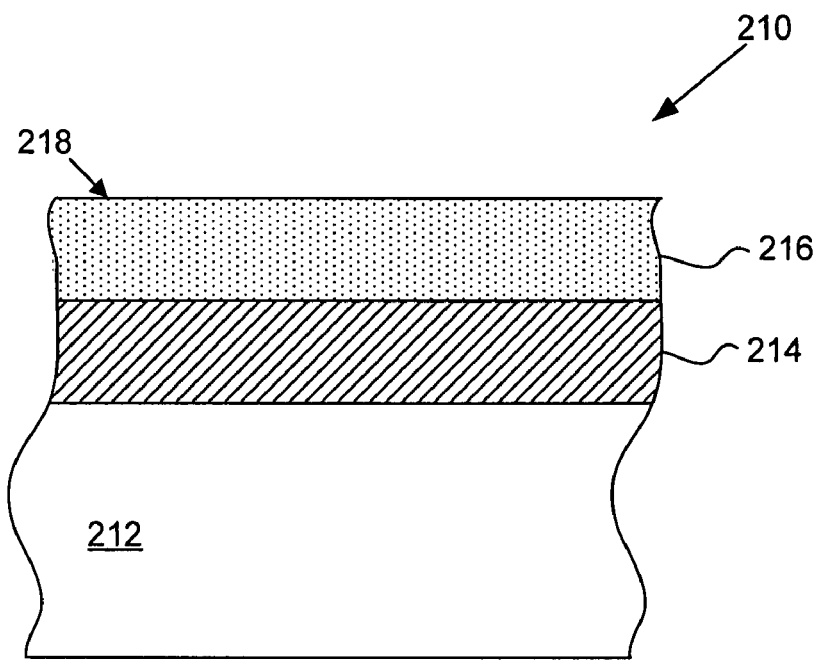
FIGS. 2A and 2B show exemplary structures corresponding to initial steps in the flowchart of FIG. 1.

Referring now to FIG. 2A, structure 210 of FIG. 2A shows a cross sectional portion of a semiconductor wafer prepared for lithographic patterning. Structure 210 shows a portion of semiconductor wafer 212, material layer 214, and layer of resist 216 having top surface 218, according to one embodiment of the invention shown in flowchart 100 of FIG. 1. In particular, structure 210 shows a portion of the semiconductor wafer before processing step 120 of flowchart 100.

Figure 2B:
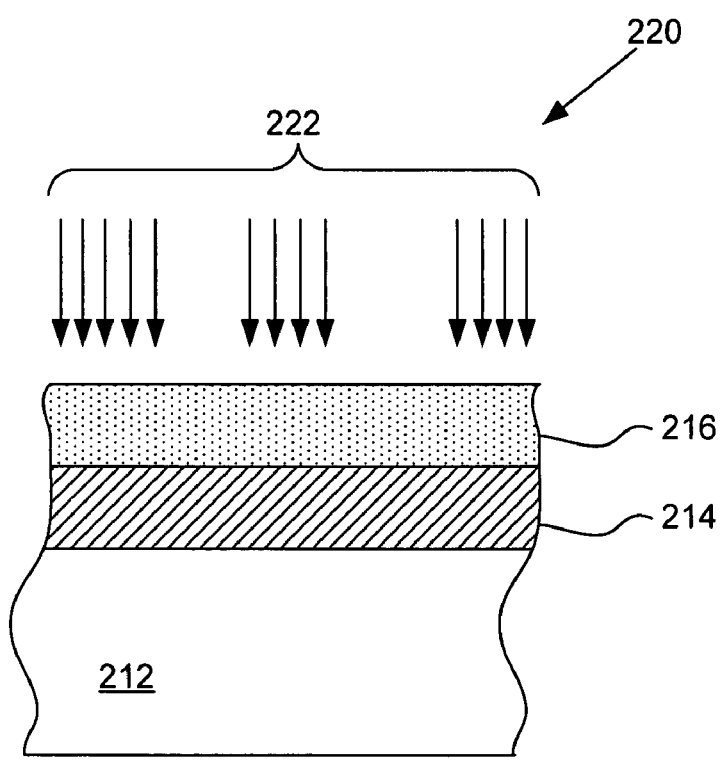
Figure 3:
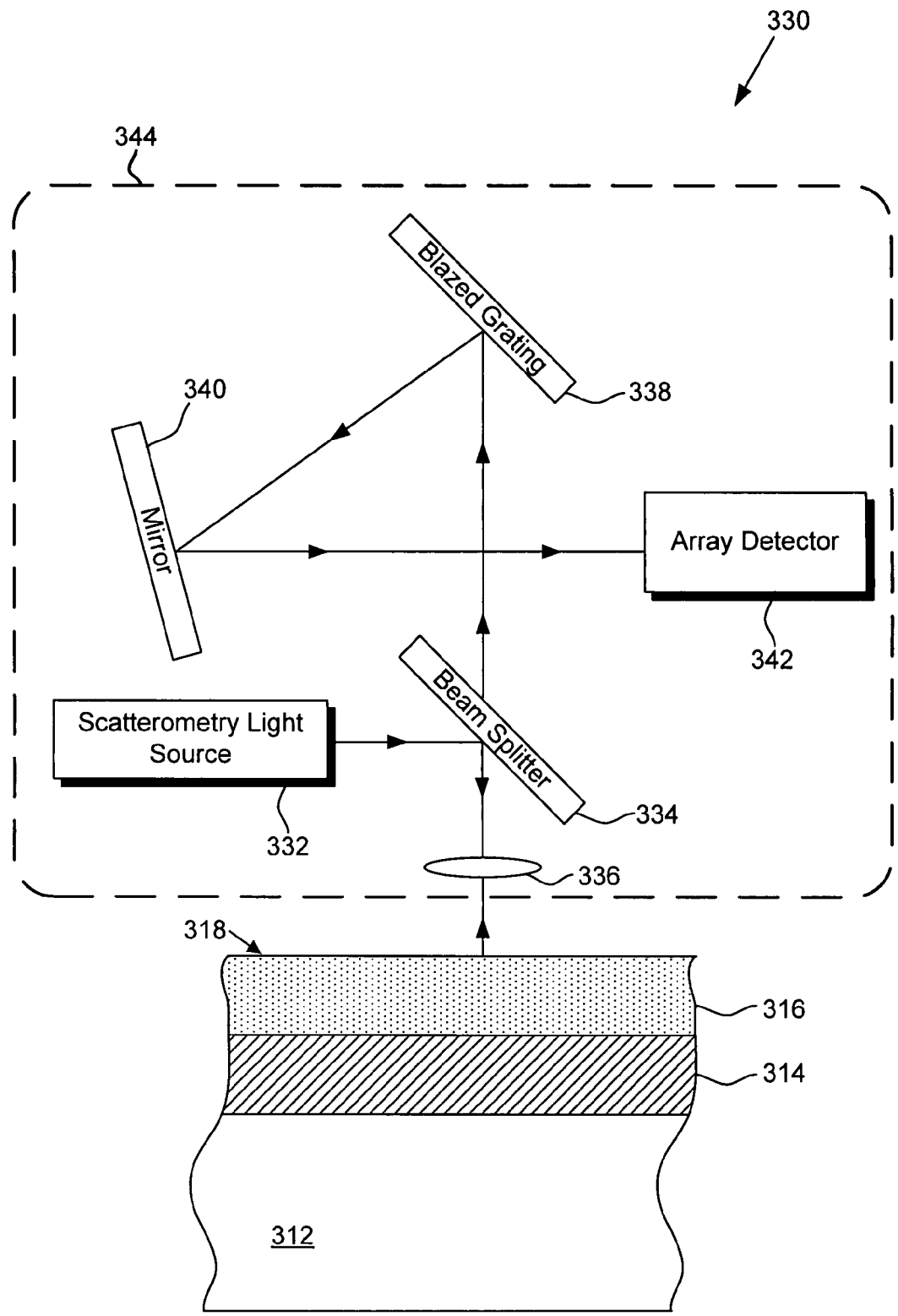
FIG. 3 shows an exemplary structure corresponding to an intermediate step in the flowchart of FIG. 1.
Figure 4:
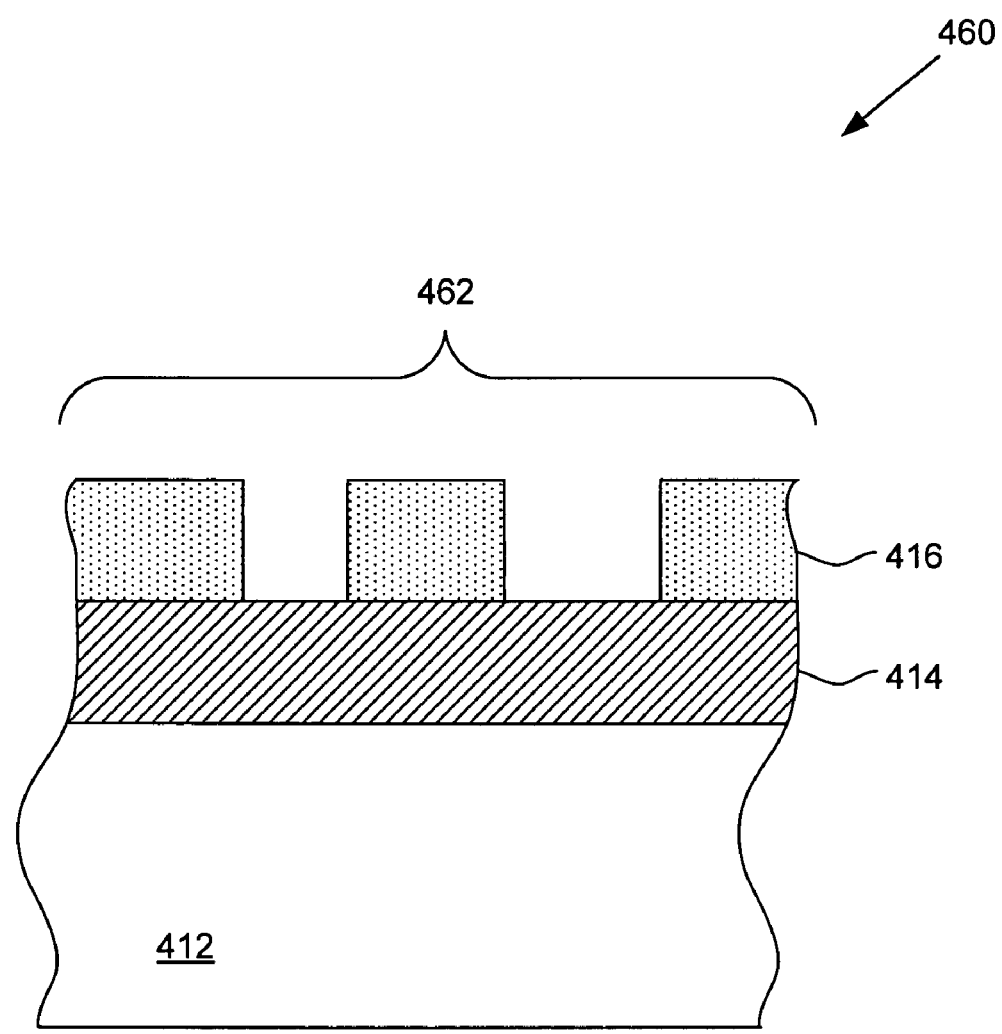
FIG. 4 shows an exemplary structure corresponding to a final step in the flowchart of FIG. 1.

Referring to FIGS. 2B, 3, and 4, structures 220, 330, and 460 show the result of performing, on structure 210, steps 120, 130, and 160 of flowchart 100 of FIG. 1, respectively. For example, structure 220 shows structure 210 during processing step 120, structure 330 shows structure 210 during processing of step 130, and so forth.

Continuing with step 110 in FIG. 1 and structure 210 in FIG. 2A, step 110 of flowchart 100 comprises formation of layer of resist 216 over material layer 214, situated over semiconductor wafer 212. Material layer 214 can comprise a conductive material, such as polysilicon, aluminum, or copper, or a dielectric material, such as silicon dioxide or silicon nitride, for example. In other embodiments, there may be more than one material layer, and those additional material layers between material layer 214 and semiconductor wafer 212 may include additional patterns, for example, circuits or connective traces.

In one embodiment, layer of resist 216 may comprise a polymer matrix and one or more catalytic species. The polymer matrix can comprise an organic polymer material comprising styrene, acrylate, or methacrylate monomers, for example. In other embodiments, resist 216 can comprise different organic or inorganic polymers. Catalytic species present in layer of resist 216 may be, for example, an acid, base, or oxidizing agent, activated by exposure to patterned radiation. Layer of resist 216 can be formed over material layer 214 by using a spin coat process or other suitable deposition process, as known in the art.

At step 120 in FIG. 1 and structure 220 in FIG. 2B, layer of resist 216 is exposed to patterned radiation 222 under vacuum conditions in a lithographic tool in a lithographic process. During the lithographic process, a pattern on a lithographic mask (not shown) can be transferred to layer of resist 216 formed over semiconductor wafer 212 by utilizing a low intensity radiation source, such as an extreme ultraviolet (EUV) light source. In another embodiment, an electron beam, or an ion beam may provide patterned radiation 222, for example.

Following step 120 in FIG. 1, a vacuum environment is not required to perform the remaining process steps of flowchart 100, according to the present embodiment. For example, while the remaining process steps of flowchart 100 can be performed in a vacuum environment, they may alternatively be performed in a non-vacuum environment, such as air. However, the remaining process steps of flowchart 100 may also be performed in nitrogen, oxygen, or other suitable type of environment, for example.

Continuing with step 130 of flowchart 100 and structure 330 in FIG. 3, step 130 of flowchart 100 comprises determining the suitability of layer of resist 316 for semiconductor wafer fabrication, by means of a scatterometry process performed on layer of resist 316. As shown in FIG. 3, structure 330 includes layer of resist 316 having top surface 318, material layer 314, and semiconductor wafer 312, corresponding respectively to resist 216, top surface 218, material layer 214, and semiconductor wafer 212, in FIG. 2A. Also shown in FIG. 3 is scatterometer 344, comprising scatterometry light source 332, beam splitter 334, lens assembly 336, blazed grating 338, mirror 340, and array detector 342, having no analogues in previous figures. Scatterometer 344 in FIG. 3 is a conceptual block diagram, presented for the purpose of providing an overview. Elements included in scatterometer 344 are conceptual representations of physical and optical elements, and are thus not intended to show dimensions or relative sizes or scale. Moreover, it is noted that scatterometer 344 may contain additional elements, which are not shown in FIG. 3 for purposes of brevity and simplicity of illustration.

By way of background, scatterometry is a procedure for measuring the characteristics of a surface by comparing light scattered from the surface, to unscattered reference light from the same emission source. Changes in wavelength and polarization of the scattered light, compared to the unscattered reference light, reveals characteristics of the material being measured. Scatterometry is typically used as a metrology tool in the semiconductor fabrication arts, to confirm dimensions, for example line width, on a developed lithographic pattern. In its conventional use, scatterometry is typically performed in the latter stages of semiconductor fabrication.

Unlike conventional use of scatterometry as a post hoc quality control measure, the present application introduces a method for utilizing this procedure as an assessment tool at an earlier stage in semiconductor wafer fabrication. According to the present embodiment, scatterometry is performed after exposure to patterned radiation, but before development of the lithographic pattern.

Referring to FIG. 3, structure 330 includes scatterometer 344 for determining suitability of layer of resist 316 for semiconductor wafer fabrication after step 120 of Flowchart 100 in FIG. 1, in which the resist is exposed to patterned radiation. In FIG. 3, corresponding to step 130 in FIG. 1, light emitted from scatterometry light source 332 (not to be confused with lithographic light source providing patterned radiation in previous step 120 of FIG. 1) encounters beam splitter 334. A portion of the light emitted by scatterometry light source 332 is directed from scatterometer 344 to layer of resist 316 through lens assembly 336, after encountering beam splitter 334. Another portion of the light emitted by scatterometry light source 332 is diverted by beam splitter 334, re-directed by blazed grating 338, and reflected by mirror 340, into array detector 342. There, light scattered from layer of resist 316 and received by array detector 342 is compared to the unscattered portion of light emitted by scatterometry light source 332, in a metrology procedure well known in the art.

As shown in FIG. 3, in the present embodiment scatterometer 344 is represented as a normal incidence measurement tool. In another embodiment, however, light from scatterometry light source 332 may be incident upon top surface 318 of layer of resist 316 at a suitable angle for scattered light to be received by correspondingly situated array detector 342.

Scatterometry performed on layer of resist 316 in step 130 of flowchart 100 provides information about layer of resist 316 in the aftermath of exposure to patterned radiation in step 120. Measurements made during the scatterometry procedure at step 130 can reveal whether layer of resist 316 is suitable for semiconductor wafer fabrication, and may indicate, for instance, whether a subject fabrication process should continue or be re-initiated. Scatterometry may reveal the extent of out-gassing of layer of resist 316 during lithographic exposure, for example, or the extent and quality of the response of a catalytic species within the resist material, to exposure to patterned radiation in step 120. By measuring resist characteristics before development of a lithographic pattern, and determining suitability of the resist at that point in the fabrication process, the present embodiment enables more efficient and cost effective semiconductor wafer fabrication due to the savings of time and resources otherwise dedicated to performing the intervening processing steps, for example.

Consequently, at step 140 of flowchart 100 in FIG. 1, a decision can be made, based on the scatterometric assessment (i.e. determination) performed in step 130, as to whether layer of resist 316 in FIG. 3 is suitable for semiconductor wafer fabrication. Referring to both FIG. 3 and flowchart 100 in FIG. 1, if the assessment (i.e. determination) performed at step 130 of flowchart 100 reveals that layer of resist 316 possesses characteristics that comply with suitability specifications and tolerances, fabrication of semiconductor wafer 312 may proceed. If, however, the assessment at step 130 reveals deviations from desired specifications sufficient to render layer of resist 316 unsuitable for fabrication of semiconductor wafer 312, the fabrication process can be discontinued at that intermediate stage, and a new layer of resist may be formed on the semiconductor wafer as in step 110 of flowchart 100. Implemented as described above, the present embodiment may be utilized as a process control method during semiconductor wafer fabrication, for instance. In another embodiment, the present invention may be utilized as a method for selecting amongst alternative resist compositions, for example, when evaluating new or competing resists formed on test wafers.

Returning to FIG. 1, at step 150 of flowchart 100, the semiconductor wafer including the layer of resist is heated in a post exposure bake process. In the embodiment in flowchart 100, the post exposure bake process can accelerate the transformation of exposed areas of the layer of resist, by accelerating the chemical processes activated by exposure to patterned radiation in step 120, and well known in the art. Although in the present embodiment, post exposure bake step 150 occurs after scatterometric assessment (i.e. determination) step 130, in one embodiment the post exposure bake step precedes the scatterometric determination step.

Continuing with step 160 of flowchart 100 and structure 460 in FIG. 4, a resist pattern is created corresponding to the patterned radiation delivered in step 120. Structure 460 comprises layer of resist 416, material layer 414, and semiconductor wafer 412, corresponding respectively to layer of resist 216, material layer 214, and semiconductor wafer 212, in FIG. 2A. Also shown in FIG. 4 is pattern 462 formed on layer of resist 416 after assessment of layer of resist 416 by the scatterometry process of step 130. Pattern 462 can be created by application of a developing reagent to the resist material in any suitable developing process, as known in the art. In the developing process, the resist can be immersed in a solution containing dissolution reagent, for example.

As a result of the method for assessing and determining suitability of a resist for semiconductor wafer fabrication described in the exemplary embodiments set forth in the present application and shown by flowchart 100 in FIG. 1, a semiconductor wafer having one or more semiconductor dies is fabricated. In a subsequent step (not shown on flowchart 100) the semiconductor dies can be separated from the semiconductor wafer in a dicing process after semiconductor wafer fabrication has been completed. The fabricated and separated semiconductor die, which is fabricated by using the present invention's method for determining suitability of a resist for semiconductor wafer fabrication, can be utilized on a circuit board, for example. The diced and separate dies can be packaged, i.e. can be enclosed and/or sealed in suitable semiconductor packages, as known in the art.

Figure 5:
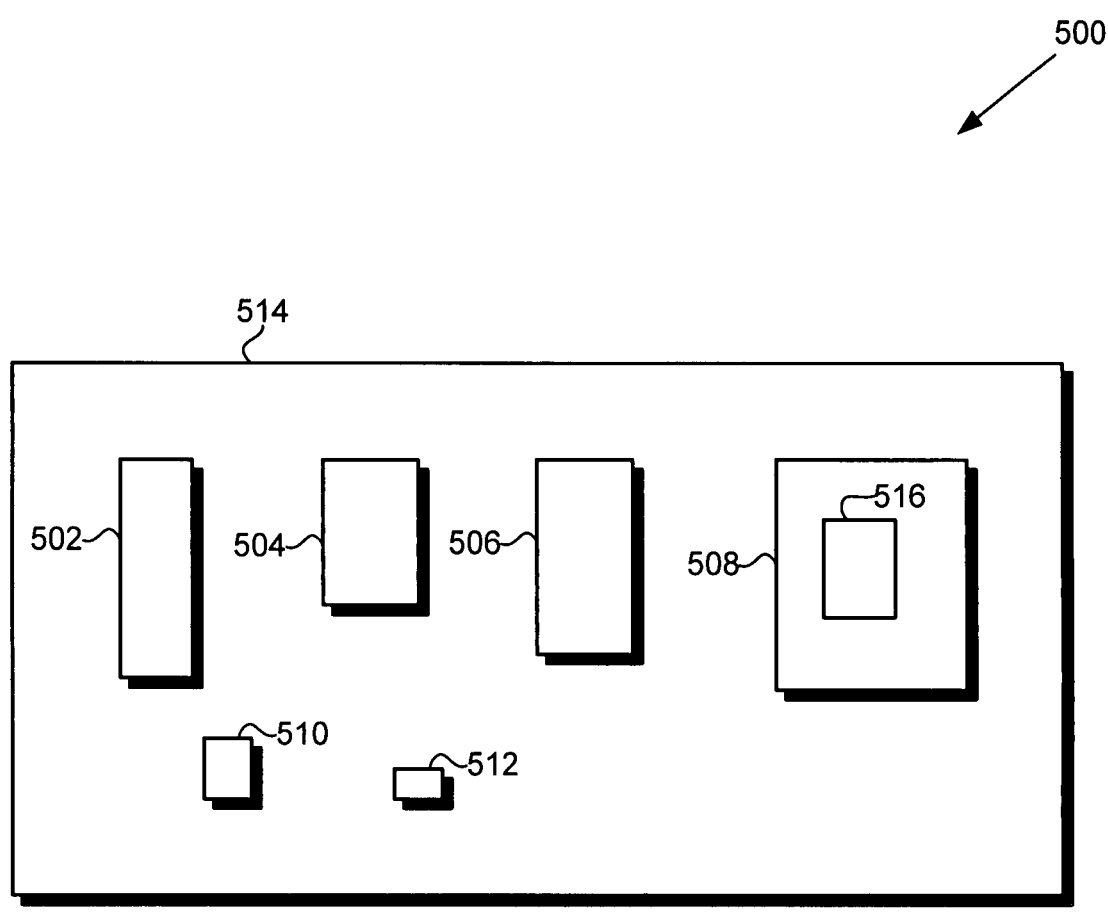
FIG. 5 is a diagram of an exemplary electronic system including an exemplary chip or die fabricated using a method for determining suitability of a resist in semiconductor wafer fabrication, in accordance with one or more embodiments of the present invention.

FIG. 5 is a diagram of an exemplary electronic system including an exemplary chip or die fabricated by using the present invention's method for assessing and determining suitability of a resist for semiconductor wafer fabrication, in accordance with one or more embodiments of the present invention. Electronic system 500 includes exemplary modules 502, 504, and 506, IC chip 508, discrete components 510 and 512, residing in and interconnected through circuit board 514. In one embodiment, electronic system 500 may include more than one circuit board. IC chip 508 can comprise a semiconductor die, which is fabricated by using an embodiment of the invention's method for determining suitability of a resist for semiconductor wafer fabrication. IC chip 508 includes circuit 516, which can be a microprocessor, for example.

As shown in FIG. 5, modules 502, 504, and 506 are mounted on circuit board 514 and can each be, for example, a central processing unit (CPU), a graphics controller, a digital signal processor (DSP), an application specific integrated circuit (ASIC), a video processing module, an audio processing module, an RF receiver, an RF transmitter, an image sensor module, a power control module, an electro-mechanical motor control module, or a field programmable gate array (FPGA), or any other kind of module utilized in modern electronic circuit boards. Circuit board 514 can include a number of interconnect traces (not shown in FIG. 5) for interconnecting modules 502, 504, and 506, discrete components 510 and 512, and IC chip 508.

Also shown in FIG. 5, IC chip 508 is mounted on circuit board 514 and can comprise, for example, any semiconductor die that is fabricated by utilizing an embodiment of the invention's method for assessing and determining suitability of a resist for semiconductor wafer fabrication. In one embodiment, IC chip 508 may not be mounted on circuit board 514, and may be interconnected with other modules on different circuit boards. Further shown in FIG. 5, discrete components 510 and 512 are mounted on circuit board 514 and can each be, for example, a discrete filter, such as one including a BAW or SAW filter or the like, a power amplifier or an operational amplifier, a semiconductor device, such as a transistor or a diode or the like, an antenna element, an inductor, a capacitor, or a resistor.

Electronic system 500 can be utilized in, for example, a wired communications device, a wireless communications device, a cell phone, a switching device, a router, a repeater, a codec, a LAN, a WLAN, a Bluetooth enabled device, a digital camera, a digital audio player and/or recorder, a digital video player and/or recorder, a computer, a monitor, a television set, a satellite set top box, a cable modem, a digital automotive control system, a digitally-controlled home appliance, a printer, a copier, a digital audio or video receiver, an RF transceiver, a personal digital assistant (PDA), a digital game playing device, a digital testing and/or measuring device, a digital avionics device, a medical device, or a digitally-controlled medical equipment, or in any other kind of system, device, component or module utilized in modern electronics applications.

Thus, the invention's method for determining suitability of a resist for semiconductor wafer fabrication advantageously improves the efficiency and cost effectiveness of semiconductor wafer fabrication. By determining the suitability of a layer of resist using scatterometry following exposure to patterned radiation at an early stage of fabrication, the present invention enables early determination of the suitability of a layer of resist, or of a particular resist composition. The early determination of resist suitability made possible by the present invention avoids the consumption of time, expense, and other resources associated with the conventional approach in which the determination occurs after development of a lithographic pattern transferred to the resist.

From the above description of the invention it is manifest that various techniques can be used for implementing the concepts of the present invention without departing from its scope. Moreover, while the invention has been described with specific reference to certain embodiments, a person of ordinary skill in the art would appreciate that changes can be made in form and detail without departing from the spirit and the scope of the invention. Thus, the described embodiments are to be considered in all respects as illustrative and not restrictive. It should also be understood that the invention is not limited to the particular embodiments described herein but is capable of many rearrangements, modifications, and substitutions without departing from the scope of the invention.

Thus, a method for determining suitability of a resist in semiconductor wafer fabrication has been described.

The invention claimed is:

1. A method for determining suitability of a layer of resist for semiconductor fabrication, said method comprising:
   forming said layer of resist over a semiconductor wafer;
   exposing said layer of resist to a patterned radiation;
   using a scatterometry process to determine said suitability of said layer of resist prior to developing a pattern on said layer of resist.

2. The method of claim 1, further comprising heating said layer of resist in a post exposure bake process.

3. The method of claim 2 wherein said scatterometry process precedes said post exposure bake process.

4. The method of claim 1 wherein said using said scatterometry process determines out-gassing of said layer of resist during exposure to said patterned radiation.

5. The method of claim 1 wherein said using said scatterometry process determines a response of components within said layer of resist to exposure to said patterned radiation.

6. The method of claim 1 further comprising developing said layer of resist.

7. The method of claim 1, further comprising dicing said semiconductor wafer into a plurality of semiconductor dies.

8. The method of claim 7, further comprising utilizing one or more of said plurality of semiconductor dies in a circuit board.

9. The method of claim 7, further comprising packaging one or more of said plurality of semiconductor dies.

10. The method of claim 7, wherein one or more of said plurality of semiconductor dies are utilized in a circuit board as a part of an electronic system, said electronic system being selected from the group consisting of a wired communications device, a wireless communications device, a cell phone, a switching device, a router, a repeater, a codec, a LAN, a WLAN, a Bluetooth enabled device, a digital camera, a digital audio player and/or recorder, a digital video player and/or recorder, a computer, a monitor, a television set, a satellite set top box, a cable modem, a digital automotive control system, a digitally-controlled home appliance, a printer, a copier, a digital audio or video receiver, an RF transceiver, a personal digital assistant (PDA), a digital game playing device, a digital testing and/or measuring device, a digital avionics device, a medical device, and a digitally-controlled medical equipment.

11. A method of process control for use in fabrication of a semiconductor wafer, said method comprising:
   forming a layer of resist over said semiconductor wafer;
   exposing said layer of resist to a patterned radiation in a lithographic process;
   determining a suitability of said layer of resist for fabrication of said semiconductor wafer by using a scatterometry process;
   developing said layer of resist if said determining reveals said suitability for fabrication of said semiconductor wafer.

12. The method of claim 11 wherein said exposing to said patterned radiation comprises exposure to extreme ultraviolet (EUV) light.

13. The method of claim 11 wherein said exposing to said patterned radiation comprises exposure to an electron beam.

14. The method of claim 11 wherein said exposing to said patterned radiation comprises exposure to an ion beam.

15. The method of claim 11, further comprising dicing said semiconductor wafer into a plurality of semiconductor dies.

16. The method of claim 15, further comprising utilizing one or more of said plurality of semiconductor dies in a circuit board.

17. The method of claim 15, further comprising packaging one or more of said plurality of semiconductor dies.

18. The method of claim 15, wherein one or more of said plurality of semiconductor dies are utilized in a circuit board as a part of an electronic system, said electronic system being selected from the group consisting of a wired communications device, a wireless communications device, a cell phone, a switching device, a router, a repeater, a codec, a LAN, a WLAN, a Bluetooth enabled device, a digital camera, a digital audio player and/or recorder, a digital video player and/or recorder, a computer, a monitor, a television set, a satellite set top box, a cable modem, a digital automotive control system, a digitally-controlled home appliance, a printer, a copier, a digital audio or video receiver, an RF transceiver, a personal digital assistant (PDA), a digital game playing device, a digital testing and/or measuring device, a digital avionics device, a medical device, and a digitally-controlled medical equipment.

19. The method of claim 11, further comprising heating said layer of resist in a post exposure bake process.

* * * * *